United States Patent
Kajihara et al.

(10) Patent No.: US 7,273,934 B2
(45) Date of Patent: Sep. 25, 2007

(54) THREE-BRANCHED SUGAR-CHAIN ASPARAGINE DERIVATIVES, THE SUGAR-CHAIN ASPARAGINES, THE SUGAR CHAINS, AND PROCESSES FOR PRODUCING THESE

(75) Inventors: Yasuhiro Kajihara, 4-2-205, Ushikubohigashi 2-chome, Tsuzuki-ku, Yokohama-shi, Kanagawa 224-0014 (JP); Kazuaki Kakehi, Nara (JP); Kazuhiro Fukae, Tokushima (JP)

(73) Assignees: Otsuka Chemical Co., Ltd., Osaka (JP); Yasuhiro Kajihara, Yokohama (JP)

( * ) Notice: Subject to any disclaimer, the term of this patent is extended or adjusted under 35 U.S.C. 154(b) by 53 days.

(21) Appl. No.: 10/540,623

(22) PCT Filed: Dec. 26, 2003

(86) PCT No.: PCT/JP03/16912

§ 371 (c)(1),
(2), (4) Date: Jul. 25, 2005

(87) PCT Pub. No.: WO2004/058824

PCT Pub. Date: Jul. 15, 2004

(65) Prior Publication Data

US 2006/0009421 A1    Jan. 12, 2006

(30) Foreign Application Priority Data

Dec. 26, 2002 (JP) .............................. 2002-378203

(51) Int. Cl.
*C08B 37/00* (2006.01)
(52) U.S. Cl. ................ 536/53; 536/18.7; 536/55.3; 536/22.1
(58) Field of Classification Search ................ 536/53, 536/55.3, 18.7, 22.1; 535/18.7
See application file for complete search history.

(56) References Cited

U.S. PATENT DOCUMENTS 5,238,821 A * 8/1993 Barsomian et al. ........ 435/69.1

OTHER PUBLICATIONS

Endo et al. et al. (The Journal of Biological Chemistry (1982) vol. 257. No. 15, pp. 8755-8760).*

Lowe, Mark et al., "The Structure of the Complex Type Oligosaccharide from Rabbit Hepatic Binding Protein: A Re-Examination", *The Journal of Biological Chemistry*, vol. 258, No. 3, pp. 1885-1887, 1983.
Endo, Masahiko et al., "The Structures and Microheterogeneity of the Carbohydrate Chains of Human Plasma Ceruloplasmin: A Study Employing 500-MHz $^1$H-NMR Spectroscopy", *The Journal of Biological Chemistry*, vol. 257, No. 15, pp. 8755-8760, 1982.
Meinjohannas, Ernst et al., "Novel sequential solid-phase synthesis of N-linked glycopeptides from natural sources", *J. Chem. Soc., Perkin Trans.*, 1, 1998, pp. 549-260.

* cited by examiner

*Primary Examiner*—Shaojia Anna Jiang
*Assistant Examiner*—Michael C. Henry
(74) *Attorney, Agent, or Firm*—Kubovcik & Kubovcik

(57) ABSTRACT

A 3-branched asparagine-linked oligosaccharide derivative of the formula (1) wherein the nitrogen of amino group of asparagine is modified with a lipophilic protective group, biotin group or FITC group; a 3-branched asparagine-linked oligosaccharide derivative which contains at least one fucose in N-acetylglucosamine on the nonreducing terminal side of the asparagine-linked oligosaccharide of the derivative; asparagine-linked oligosaccharides and oligosaccharides thereof

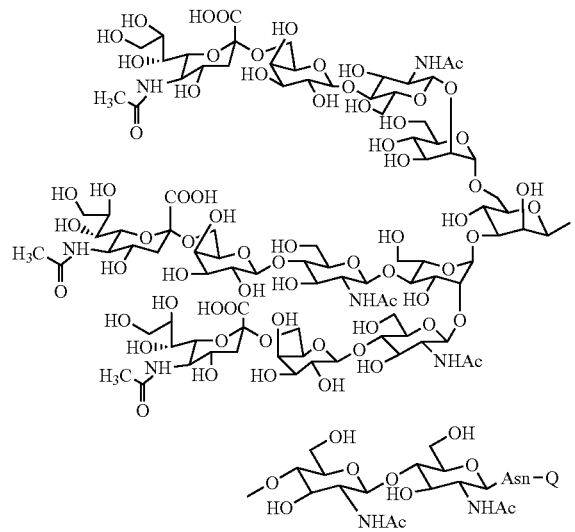

wherein Q is a lipophilic protective group, biotin group or FITC group.

9 Claims, No Drawings

THREE-BRANCHED SUGAR-CHAIN ASPARAGINE DERIVATIVES, THE SUGAR-CHAIN ASPARAGINES, THE SUGAR CHAINS, AND PROCESSES FOR PRODUCING THESE

This application is a 371 of international application PCT/JP2003/016912, filed Dec. 26, 2003, which claims priority based on Japanese patent application No. 2002-378203 filed Dec. 26, 2002.

TECHNICAL FIELD

The present invention relates to 3-branched asparagine-linked oligosaccharide derivatives, 3-branched asparagine-linked oligosaccharides, 3-branched oligosaccharides and processes for preparing such compounds.

BACKGROUND ART

In recent years, molecules of oligosaccharides have attracted attention as third chain life molecules following nucleic acids (DNA) and proteins. The human body is a huge cell society comprising about 60 trillion cells, and the surfaces of all the cells are covered with oligosaccharide molecules. For example, ABO blood types are determined according to the difference of oligosaccharides over the surfaces of cells.

Oligosaccharides function in connection with the recognition of cells and interaction of cells and are key substances for the establishment of the cell society. Disturbances in the cell society lead, for example, to cancers, chronic diseases, infectious diseases and aging.

For example, it is known that when cells cancerate, changes occur in the structure of oligosaccharides. It is also known that *Vibrio cholerae*, influenza virus, etc. ingress into cells and cause infection by recognizing and attaching to a specific oligosaccharide.

Oligosaccharides are much more complex than DNA or proteins in structure because of the diversity of arrangements of monosaccharides, modes or sites of linkages, lengths of chains, modes of branches and overall structures of higher order. Accordingly, biological information derived from the structures thereof is more diversified than is the case with DNA and proteins. Although the importance of research on oligosaccharides has been recognized, the complexity and variety of structures thereof have delayed progress in the research on oligosaccharides unlike the studies on DNA and proteins.

E. Meinjohanns (J. Chem. Soc. Perkin Transl. 1998. pp. 549-560) et al. prepared a 2-branched asparagine-linked oligosaccharide from bovine fetuin (bovine-derived glycoprotein). They utilized a hydrazine decomposition reaction to obtain a 2-branched oligosaccharide for use as the starting material. Since hydrazine has high toxicity, the application of the oligosaccharide derivatives obtained to pharmaceuticals involves problems as to safety because of the possibility of a trace of hydrazine becoming incorporated into the derivative. 3-Branched asparagine-linked oligosaccharides still remain to be prepared.

An object of the present invention is to provide a 3-branched asparagine-linked oligosaccharide derivative wherein the nitrogen of the amino group of asparagine is modified with a lipophilic protective group, biotin group or FITC group and a process for preparing the derivative.

Another object of the invention is to provide a 3-branched asparagine-linked oligosaccharide, a 3-branched oligosaccharide and processes for preparing these compounds.

DISCLOSURE OF THE INVENTION

The present invention provides the following inventions.

1. A 3-branched asparagine-linked oligosaccharide derivative of the formula (1) wherein the nitrogen of amino group of asparagine is modified with a lipophilic protective group, biotin group or FITC group

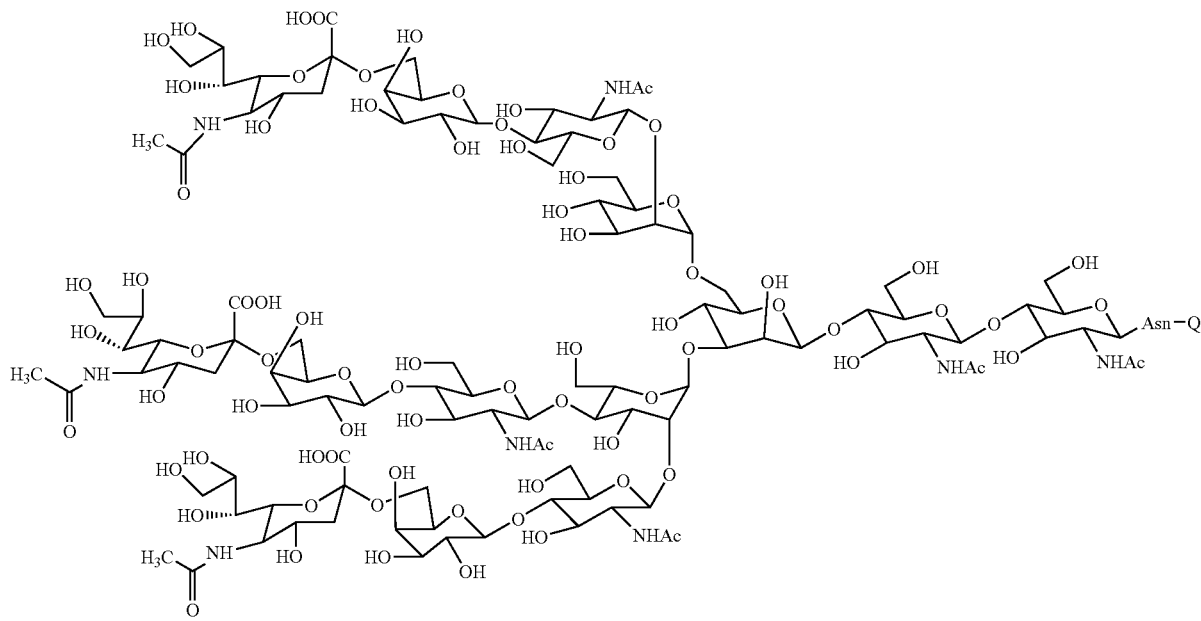

wherein Q is a lipophilic protective group, biotin group or FITC group.

2. A 3-branched asparagine-linked oligosaccharide derivative which contains at least one fucose in N-acetylglucosamine on the nonreducing terminal side of the asparagine-linked oligosaccharide of the derivative.

3. A 3-branched asparagine-linked oligosaccharide obtained by removing the lipophilic protective group, biotin group or FITC group from the above 3-branched asparagine-linked oligosaccharide derivative.

4. A 3-branched oligosaccharide obtained by removing the asparagine moiety from the above 3-branched asparagine-linked oligosaccharide.

5. A microplate having immobilized thereto the above biotinated 3-branched asparagine-linked oligosaccharide.

6. An affinity column having immobilized thereto the above biotinated 3-branched asparagine-linked oligosaccharide.

We have developed processes for preparing 3-branched asparagine-linked oligosaccharide derivatives, 3-branched asparagine-linked oligosaccharides and 3-branched oligosaccharides by which various isolated 3-branched asparagine-linked oligosaccharide derivatives can be prepared easily in large quantities from bovine fetuin (a bovine-derived glycoprotein), and further novel 3-branched asparagine-linked oligosaccharide derivatives, 3-branched asparagine-linked oligosaccharides and 3-branched oligosaccharides wherein oligosaccharides deficient in sugar residue as desired are linked.

The process of the present invention for preparing a 3-branched asparagine-linked oligosaccharide derivative is principally characterized by introducing a lipophilic protective group into (or bonding the group to) 3-branched asparagine-linked oligosaccharides included, for example, among the asparagine-linked oligosaccharides derived from a natural glycoprotein, preferably, into those contained in a mixture of asparagine-linked oligosaccharides to obtain a mixture of 3-branched asparagine-linked oligosaccharide derivatives, and thereafter separating the mixture into the individual 3-branched asparagine-linked oligosaccharide derivatives. The term an "asparagine-linked oligosaccharide" as used herein refers to an oligosaccharide having asparagine linked thereto. Further the term "oligosaccharides capable of linking to asparagine" refers to a group of oligosaccharides wherein N-acetylglucosamine present at a reducing terminal is attached by N-glucoside linkage to the acid amino group of asparagine (Asn) in the polypeptide of a protein and which has Man($\beta$1-4)GlcNac($\beta$1-4)GlcNac as the core structure. The term an "asparagine-linked oligosaccharide derivative" refers to an asparagine-linked oligosaccharide wherein a lipophilic protective group is attached to asparagine moiety. Further "AcHN" in the structural formulae of compounds refers to an acetamido group.

As described-above, the oligosaccharides derived from a natural glycoprotein are a mixture of oligosaccharides which are randomly deficient in sugar residue at a nonreducing terminal. We have unexpectedly found that by introducing a lipophilic protective group into the 3-branched asparagine-linked oligosaccharides included among the oligosaccharides derived from a natural glycoprotein, more specifically, into those contained in a mixture of asparagine-linked oligosaccharides, a mixture of 3-branched asparagine-linked oligosaccharide derivatives having the protective group introduced thereinto can be easily separated into individual 3-branched asparagine-linked oligosaccharide derivatives by a known chromatographic procedure. Accordingly, 3-branched asparagine-linked oligosaccharide derivatives of the present invention can be prepared in large quantities.

Thus, individually separated 3-branched asparagine-linked oligosaccharide derivatives can be derived from a mixture of asparagine-linked oligosaccharides by introducing a lipophilic protective group into 3-branched asparagine-lined oligosaccharides. This appears attributable to the fact that the introduction of the lipophilic protective group improves the overall solubility of the 3-branched asparagine-linked oligosaccharide derivatives in fats, for example, to result in a remarkable improvement in the interaction between the derivatives and the reverse-phase column to be used favorably, consequently making it possible to separate the individual 3-branched asparagine-linked oligosaccharide derivatives by sensitively distinguishing the derivatives from the difference in the structure of oligosaccharide. For example, Fmoc group which is a lipophilic protective group suitable to use in the present invention is extremely high in solubility in fats. Stated more specifically, the fluorenyl skeleton of Fmoc group has a structure comprising two benzene rings linked to a 5-membered ring in the center and having exceedingly high fat solubility, and exhibits strong interaction, for example, with the octadecyl group of ODS column which is one of reverse-phase columns, making it possible to separate the 3-branched asparagine-linked oligosaccharide derivatives which resemble in structure.

Further according to the invention, it is possible to readily obtain large quantities of 3-branched asparagine-linked oligosaccharides by removing the protective group from the resulting 3-branched asparagine-linked oligosaccharide derivatives, and also large quantities of 3-branched oligosaccharides by removing the asparagine moiety from the 3-branched asparagine-linked oligosaccharides obtained.

The present invention provides a process for preparing a 3-branched asparagine-linked oligosaccharide derivative modified with a lipophilic protective group, the process including:

(a) the step of introducing a lipophilic protective group into one or at least two 3-branched asparagine-linked oligosaccharides as contained in a mixture thereof to obtain a 3-branched asparagine-linked oligosaccharide derivative mixture, and (b) the step of subjecting to chromatography the 3-branched asparagine-linked oligosaccharide derivative mixture or a mixture obtained by hydrolyzing the 3-branched asparagine-linked oligosaccharide derivative or derivatives contained in the 3-branched asparagine-linked oligosaccharide derivative mixture to separate the derivative or derivatives.

The mixture containing one or at least two 3-branched asparagine-linked oligosaccharides and to be used in the step (a) is not limited specifically insofar as it is a mixture containing one or at least two oligosaccharides with asparagine linked thereto. For example, the mixture can be one containing one or at least two oligosaccharides having one or a plurality of asparagines attached thereto. Especially useful is a mixture containing one or at least two oligosaccharides each having asparagine attached to a reducing terminal. The term an "oligosaccharide" as used herein refers to at least two desired monosaccharides bonded to each other.

Such a mixture of 3-branched asparagine-linked oligosaccharides can be obtained by preparing a mixture of glycoproteins and/or glycopeptides derived, preferably, from a natural material such as bovine fetuin, adding to the mixture a protease such as pronase (product of Wako Pure Chemical Industries, Ltd.) or Actinase-E (product of Kaken Pharmaceutical Co., Ltd.), or a common enzyme such as carboxypeptidase or aminopeptidase to effect a reaction under known conditions, cut off the peptide portion and obtain a reaction mixture for use as the mixture. Alternatively, the mixture can be obtained by removing components other than the asparagine-linked oligosaccharides from the reaction mixture by a known method of purification, such as gel permeation chromatography, various chromatographic procedures using, for example, an ion exchange column, or high performance liquid chromatography (HPLC).

Using the mixture thus obtained and containing 3-branched asparagine-linked oligosaccharides, a lipophilic protective group is introduced into the 3-branched asparagine-linked oligosaccharides contained therein. The protecting group is not particularly limited, and there can be used, for instance, a carbonate-based or amide-based protecting group, such as Fmoc group, t-butyloxycarbonyl (Boc) group, benzyl group, allyl group, allyloxycarbonate group, or acetyl group. From the viewpoint that the resulting 3-branched asparagine-linked oligosaccharide derivative can be immediately used in the synthesis of a desired glycopeptide, the above protecting group is preferably Fmoc group, Boc group or the like, more preferably Fmoc group. The Fmoc group is especially effective when there exists in the oligosaccharide a sugar, such as sialic acid, which is relative unstable under acidic conditions. The introduction of the protecting group may be carried out according to a known process (for instance, Protecting Groups in Organic Chemistry, John Wiley & Sons INC., New York 1991, ISBN 0-471-62301-6).

For instance, when Fmoc group is used, an appropriate amount of acetone is added to the mixture containing 3-branched asparagine-linked oligosaccharides, 9-fluorenylmethyl-N-succinimidyl carbonate and sodium hydrogencarbonate are further added thereto and dissolved, and thereafter the resulting mixture is subjected to a binding reaction of Fmoc group to an asparagine moiety at 25° C., whereby the Fmoc group can be introduced into the asparagine moiety of the above 3-branched asparagine-linked oligosaccharide.

According to the procedures described above, a mixture of 3-branched asparagine-linked oligosaccharide derivatives into which a lipophilic protecting group is introduced is obtained.

The resulting mixture of 3-branched asparagine-linked oligosaccharide derivatives having the lipophilic protective group introduced thereinto is then subjected to known chromatography, especially to fractionating chromatography, to separate the derivatives individually. The separation of the derivatives by chromatography can be done by suitably using a known single chromatographic method or combination of such chromatographic methods.

For instance, the resulting mixture of 3-branched asparagine-linked oligosaccharide derivatives is purified by a gel filtration column chromatography, and then purified by using HPLC. The column which can be used in HPLC is preferably a reverse phase column, for instance, ODS, phenyl-based, nitrile-based, or anion exchange-based column, and concretely, a monoQ column manufactured by Pharmacia, Iatro-beads column manufactured by Iatron can be utilized. The separation conditions and the like may be adjusted by referring to a known condition. According to the above procedures, each of the desired 3-branched asparagine-linked oligosaccharide derivatives can be obtained from the mixture of 3-branched asparagine-linked oligosaccharide derivatives.

3-Branched asparagine-linked oligosaccharide derivatives having a desired sugar chain structure can be obtained by transferring sugars (e.g., fucose) to the various 3-branched asparagine-linked oligosaccharide derivatives obtained above with a glycosyltransferase. For example, transfer of fucose with a glycosyltransferase affords a 3-branched aspargine-linked oligosaccharide derivative having a desired sugar chain structure containing fucose. Further 3-branched asparagine-linked oligosaccharide derivatives having desired sugar chain structures and different in mode of linkage can be obtained using different glycosyltransferases.

The fucose to be used is one generally available commercially, or one prepared by chemical synthesis.

Examples of fucose transferases usable are those generally available commercially, those naturally occurring and those prepared by genetic recombination. A suitable fucos transferase can be selected in accordance with the kind of fucose to be transferred. A more specific example is Fucosyltransferase V (human recombinant, plasma-derived, serum-derived, milk-derived or liver-derived) which is an enzyme for transferring fucose to N-acetylglucosamine on the nonreducing terminal of asparagine-linked oligosaccharides. Alternatively, fucose can be transferred using fucosidase and shifting equilibrium as by pH adjustment.

The present invention further provides a process for preparing various isolated 3-branched asparagine-linked oligosaccharides in large quantities. This process includes, subsequently to the step of preparing 3-branched asparagine-linked oligosaccharide derivative or derivatives of the foregoing process for preparing such derivative, the step of removing the protective group from the resulting 3-branched asparagine-linked oligosaccharide derivative or derivatives.

The removal of the protecting group from the asparagine-linked oligosaccharide derivative can be carried out in accordance with a known process (for instance, see Protecting Groups in Organic Chemistry, John Wiley & Sons INC., New York 1991, ISBN 0-471-62301-6). For instance, when the protecting group is Fmoc group, the Fmoc group can be removed by adding morpholine to the 3-branched asparagine-linked oligosaccharide derivative in N,N-dimethylformamide (DMF) to carry out the reaction. On the other hand, Boc group can be removed by a reaction with a weak acid. After the removal of the protecting group, a 3-branched asparagine-linked oligosaccharide may be properly obtained by purifying a reaction mixture by a known process such as various chromatographies employing a gel filtration column, an ion exchange column or the like or a process of separation by HPLC as desired.

In case the protecting group is a benzyl group, the removal of the benzyl group from the asparagine-linked oligosaccharide derivative can be carried out in accordance with a known process (for instance, see Protecting Groups in Organic Chemistry, John Wiley & Sons INC., New York 1991, ISBN 0-471-62301-6).

The present invention provides an asparagine-linked oligosaccharide wherein a 3-branched asparagine-linked oligosaccharide has a biotinated or FITC-bonded amino group nitrogen atom.

The term "biotination" refers to the formation of an amide bond by the reaction of the amino group of 3-branched asparagine-linked oligosaccharide with the carboxyl group of biotin (vitamin H).

The term "FITC bonding," refers to the formation of isothioamide bond by the reaction of the amino group of 3-branched asparagine-linked oligosaccharide with the isothiocyanate group of fluorescein isothiocyanate (FITC).

The invention also provides a process for preparing an asparagine-linked oligosaccharide wherein a 3-branched asparagine-linked oligosaccharide has a biotinated or FITC-bonded amino group nitrogen atom.

The process for preparing a biotinated or FITC-bonded asparagine-linked oligosaccharide can be practiced, for example, by biotinating or bonding to FITC the amino group nitrogen of asparagine in the 3-branched asparagine-linked oligosaccharide isolated as described above.

The biotination of the invention can be effected by a known process. A biotinated 3-branched asparagine-linked oligosaccharide can be obtained, for example, by dissolving a 3-branched asparagine-linked oligosaccharide in water, adding sodium bicarbonate to the solution, adding dimethylformamide having D-(+)-biotinylsuccinimide dissolved therein to the mixture, reacting the resulting mixture at room temperature for 20 minutes, and purifying the reaction mixture by a gel permeation column or the like.

The present invention provides a microplate having a biotinated 3-branched asparagine-linked oligosaccharide immobilized thereto. The microplate can be produced by reacting a biotinated 3-branched asparagine-linked oligosaccharide with an avidinated microplate (e.g., product of Pierce) commercially available.

The invention also provides an affinity column having immobilized thereto a biotinated 3-branched asparagine-linked oligosaccharide. The column can be produced by reacting a biotinated 3-branched asparagine-linked oligosaccharide with an avidinated affinity column commercially available.

A 3-branched asparagine-linked oligosaccharide can be bonded to FITC according to the invention by a known process, for example, by dissolving the 3-branched asparagine-linked oligosaccharide in water, adding acetone and sodium bicarbonate to the solution, adding fluorescein isothiocyanate to the mixture, reacting the resulting mixture at room temperature for 2 hours, and purifying the reaction mixture such as by gel permeation column.

The FITC-bonded 3-branched asparagine-linked oligosaccharide obtained by the invention is useful for the research on acceptors of saccharides in the living body tissues and for the research on the sugar bond specificity of lectin.

The removal of the asparagine moiety from the 3-branched asparagine-linked oligosaccharide can be carried out in accordance with a known process. For instance, the 3-branched asparagine-linked oligosaccharide is reacted with anhydrous hydrazine and then acetylated to remove the asparagine moiety, whereby 3-branched oligosaccharide can be obtained. Also, 3-branched oligosaccharide can be also obtained by refluxing the 3-branched asparagine-linked oligosaccharide with heating in a basic aqueous solution and thereafter acetylating the 3-branched asparagine-linked oligosaccharide to remove the asparagine moiety. After the removal of the asparagine moiety, the oligosaccharide may be purified appropriately by a known process such as various chromatographies employing a gel filtration column, an ion exchange column or the like, and a separation process by HPLC as desired.

As described above, according to the present invention, the 3-branched asparagine-linked oligosaccharide derivative, the 3-branched asparagine-linked oligosaccharide and the 3-branched oligosaccharide (hereinafter these three terms are collectively referred to as "oligosaccharide series" in some case) each having a desired oligosaccharide structure can be prepared at a low cost, efficiently and in a large amount.

The oligosaccharide series of the invention are very useful in the field of development of pharmaceuticals. For example, vaccines for cancers are an example of application to the development of drugs. It is known that cells developing cancer produce an oligosaccharide which is not found in the living body. It is also known that when chemically prepared and given to the human body as a vaccine, such an oligosaccharide inhibits the growth of cancer. If the desired oligosaccharide series can be produced according to the invention, it is possible to prepare a vaccine which is effective for treating cancer. The oligosaccharide series obtained by the invention can further be made into derivatives by attaching novel sugar residues thereto through combinations of chemical reactions and reactions of sugar transferases for the preparation of novel vaccines.

While for example, erythropoietin (EPO) which is a glycoprotein is used as a drug for treating anemia because of the ability thereof to proliferate erythrocytes, it has been found that EPO fails to exhibit activity when having no oligosaccharide bonded thereto. Thus, proteins include those exhibiting physiological activity when having an oligosaccharide bonded thereto, so that it is possible to prepare a protein in a large quantity by an *E. coli* expression system which is incapable of bonding oligosaccharides to the protein, and subsequently introducing an oligosaccharide prepared by the invention and having a desired structure into the protein for causing the protein to exhibit a physiological activity. Alternatively, a novel glycoprotein having novel physiological activity can be synthesized by introducing 3-branched oligosaccharides prepared by the invention and having various structures into a desired protein.

Furthermore, oligosaccharides present in natural glycoproteins can be replaced with 3-branched oligosaccharides prepared by the invention to thereby give novel physiological activity to the glycoprotein. Useful as a technique for replacing the oligosaccharide present in glycoproteins by the 3-branched oligosaccharide obtained by the invention is, for example, the process disclosed in P. Sears and C. H. Wong, Science, 2001, vol. 291, pp. 2344-2350. With this process, the glycoprotein is treated with β-N-acetylglucosamimidase (Endo-M) so as to permit only one N-acetylglucosamine moiety to remain bonded to the asparagine moiety on the surface of the glycoprotein. Subsequently, a desired 3-branched oligosaccharide obtained by the invention is bonded to the N-acetylglucosamine moiety using β-N-acetylglucosaminidase (Endo-M). It is also possible to prepare a glycoprotein having N-acetylglucosamine moiety utilizing an *E. coli* expression system and using tRNA having N-acetylglucosamine bonded thereto, and to thereafter introduce a desired 3-branched oligosaccharide obtained according to the invention into the glycoprotein with use of Endo-M.

Presently, the use of glycoproteins as therapeutic drugs involves the problem that the glycoprotein administered is metabolized at a high rate because when sialic acid is removed from the oligosaccharide terminal of the glycoprotein in vivo, the glycoprotein is metabolized immediately in the liver. For this reason, there is a need to give the glycoprotein in a considerable amount. It is therefore possible to control the rate of metabolism in the living body and to decrease the dose of glycoprotein to be given by preparing an oligosaccharide according to the invention, with sialic acid which is difficult to remove incorporated therein at its terminal, and introducing the oligosaccharide into the contemplated glycoprotein with use of Endo-M.

BEST MODE OF CARRYING OUT THE INVENTION

The present invention will be described with reference to the following examples, but is not limited to these examples.

EXAMPLE 1

Fetuin (1 g, Sigma Corp.) was dissolved in phosphate buffer (7.0 in pH, 40 ml), and $NaN_3$ (10 mg) was thereafter added to the solution. To the mixture was added Orientase ONS (HBI Enzymes Inc, 1.5 g), and the resulting mixture was allowed to stand at 50° C. for about 12 hours. The completion of reaction was confirmed by TLC, and the reaction mixture was thereafter filtered with cerite. The filtrate was concentrated, and the concentrate was purified by gel permeation column chromatography (Sephadex G-25, 2.5×100 cm, $H_2O$). The fraction containing the desired oligosaccharide was collected, concentrated and then freeze-dried. To the resulting residue (about 300 mg) were added a Tris-hyrochloric acid-calcium chloride buffer solution (7.5 in pH, 20 ml) and $NaN_3$ (10 mg) to obtain a solution. To the solution was added Actinase E (163 mg), and the mixture was allowed to stand for 48 hours while being checked for pH at intervals of 12 hours. After the completion of reaction was confirmed by TLC, the reaction mixture was filtered with cerite, the filtrate was concentrated, and the concentrate was purified by gel permeation column chromatography (Sephadex G-25, 2.5×100 cm, H$_2$O). The fraction containing the desired oligosaccharide was collected, concentrated and then freeze-dried. To the resulting residue was added 40 mM HCl solution, and the mixture was allowed to stand at 80° C. for 1 hour and then neutralized. The reaction mixture was concentrated, and the concentrate was purified by gel permeation column chromatography (Sephadex G-25, 2.5×100 cm, H$_2$O). The fraction containing the desired oligosaccharides was collected, concentrated and then freeze-dried. The resulting residue was dissolved in water, and sodium bicarbonate was added to the solution.

Dimethylformamide containing Fmoc-OSu dissolved therein was then added to the mixture, followed by reaction at room temperature for 1 hour. After the disappearance of the material was confirmed by TLC (isopropanol:1 M ammonium acetate aqueous solution=3:2), the reaction mixture was concentrated using an evaporator. The residue was purified by gel permeation column (f 20 mm×300 mm, Sephadex G-25, water). The fraction containing the desired oligosaccharide was collected, concentrated and freeze-dried. The resulting residue was purified by a HPLC fractionating column (YMC-Pack R & D ODS, D-ODS-5-A, 20×250 mm, AN/25 mM ACONH$_4$ buffer=18/82, 7.5 ml/min, wavelength 274 nm). The peak of the main fraction eluted 35 minutes thereafter was collected, concentrated and then desalted by an ODS column. The product was freeze-dried to collect the resulting 3-branched oligosaccharide (1.0 mg, 0.42 mmole), which was then dissolved in 50 mM of cacodylic acid buffer (6.0 in pH, 250 ml), and bovine serum albumin (BSA, 1 mg) was then added to the solution. To the mixture were added CMP-sialic acid (3.9 mg, 6.1 mmoles) and alkaline phosphatase (1 ml, 25 units), and the resulting mixture was stirred uniformly. Finally, α2,6-sialyltransferase (CALBIOCHEM Inc., 100 ml) was added to the mixture, and the resulting mixture was allowed to stand at 37° C. for 36 hours. The reaction was terminated when the starting material almost disappeared while the reaction mixture was being monitored by HPLC, and the reaction mixture was filtered with a membrane filter. The filtrate was concentrated to reduce the quantity thereof and thereafter purified by a HPLC fractionating column (YMC-Pack R&D ODS, D-ODS-5-A, 20×250 mm, AN/25 mM AcONH$_4$ buffer=18/82, 7.5 ml/min., wavelength: 274 nm). The desired 3-branched trisialooligosaccharide was eluted in 11 minutes. The fraction was collected, desalted by an ODS column, concentrated and freeze-dried to obtain 250 mg of the desired product (18.5%).

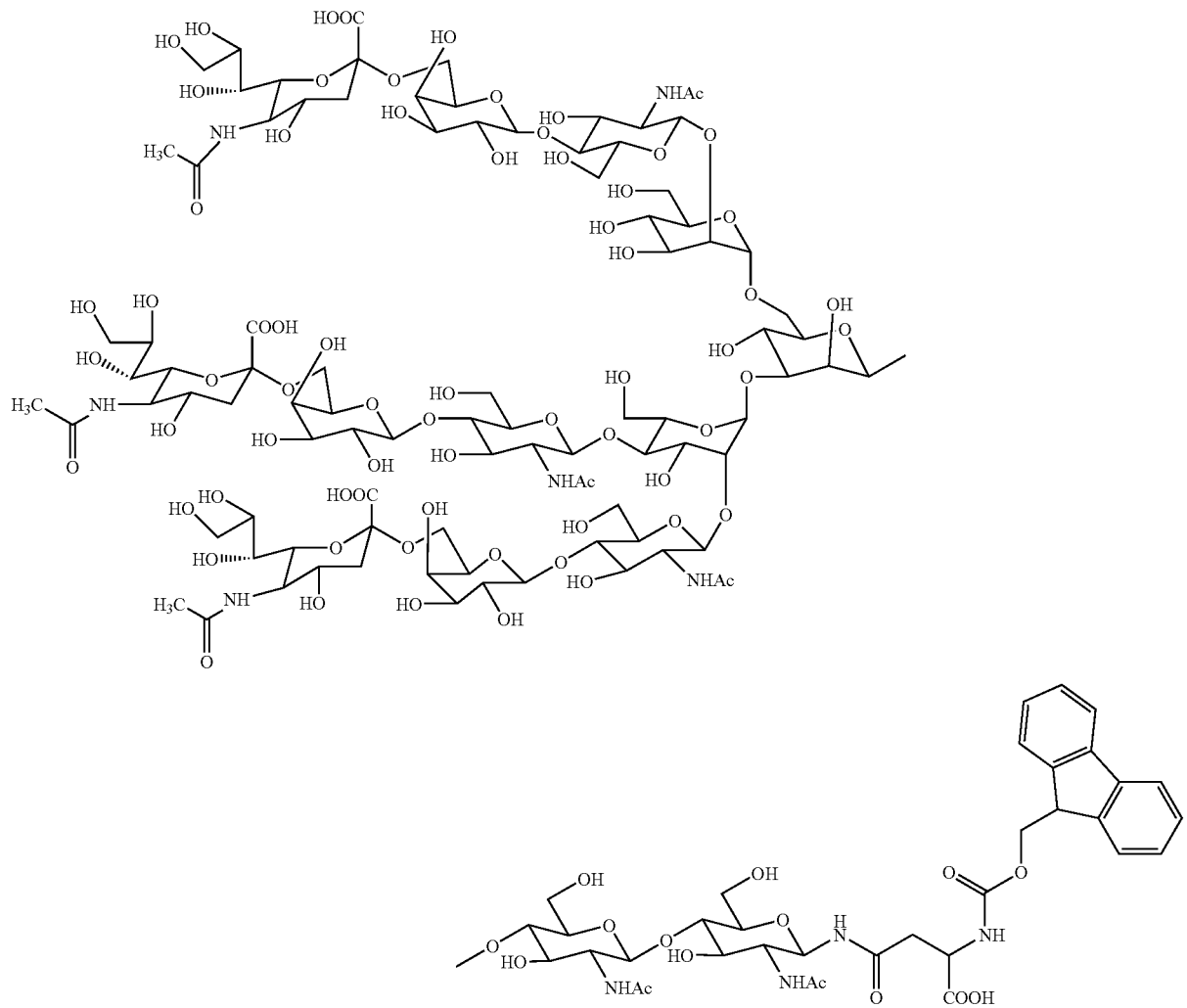

The structure of the above oligosaccharide is shown below. NeuAc: sialic acid, Gal: D-galactose, GlcNAc: N-acetylglucosamine, Man: D-mannose, Asn: asparagine

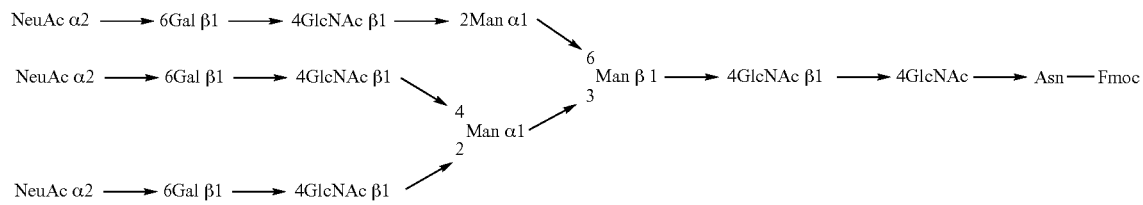

The $^1$H-NMR data for the resulting compound are as follows.

$^1$H NMR (400 MHz, D$_2$O, 30° C., HOD=4.81) d 7.90(d, 2H, Fmoc), 7.70(d, 2H, Fmoc), 7.50(dd, 2H, Fmoc), 7.42 (dd, 2H, Fmoc), 5.11(s, 1H, Man4-H1), 4.97(d, 1H, GlcNAc1-H1), 4.91(s, 1H, Man4'-H-1), 4.75(s, 1H), 4.45-4.60(m), 4.42(bd, 3H), 4.33(1H, Fmoc), 4.20(m, 3H), 4.09 (bs), 4.10(m, 2H), 2.60-2.80(m, 4H, Asn-bCH, NeuAc7,7', 7''-H3 eq), 2.40-2.60(m, 1H, Asn-bCH), 2.11, 2.08, 2.05, 2.01, 1.86(each s, Ac), 1.77(ddd, 3H, NeuAc7,7',7''-H3ax)

EXAMPLE 2

The compound prepared in Example 1 was dissolved, in an amount of 2 nmoles, in about 10 μl of Tris-hydrochloric acid buffer. To the solution were added 200 nmoles of GDP-fucose and 0.5 mU of Fucosyltransferase V (human recombinant), and the mixture was allowed to stand at 37° C. for about 2 hours for reaction. The reaction mixture was diluted with 20 μl of ultrapure water and thereafter subjected to capillary electrophoresis (fused silica capillary, 50 mm i.d., 60 cm, buffer: 100 mM Tris-borate, 8.3 in pH, 100 mM heptane sulfonate, applied voltage 27 kV, temp. 25° C., 214 nm) for separation to obtain a 3-branched asparagine-linked oligosaccharide derivative containing fucose.

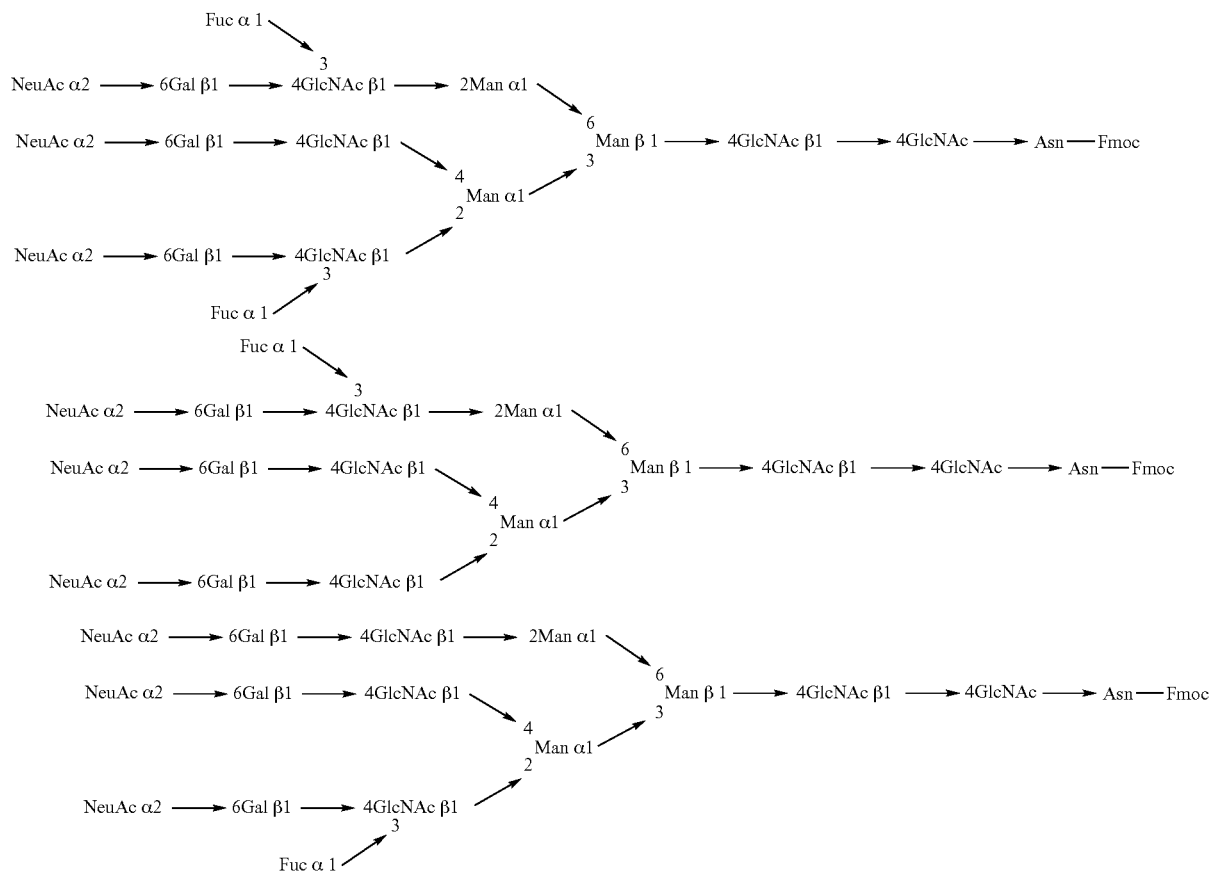

EXAMPLE 3

Biotination

First, 240 μL of N,N-dimethylformamide and 160 μL of morpholine were added to the asparagine-linked oligosaccharide Fmoc compound obtained in Example 1 per μmole of the latter, and the mixture was reacted at room temperature in an argon atmosphere. The completion of reaction was confirmed by TLC (developer solvent used: 1 M ammonium acetate:isopropanol=8:5), and the reaction mixture was cooled with ice water. To the reaction mixture was added diethyl ether in 10 times the amount of the mixture, followed by stirring for 15 minutes, and the precipitate separating out was filtered off. The residue obtained was dissolved in water, and the solution was evaporated at 35° C. With addition of 3 mL of toluene, the resulting residue was further evaporated. This procedure was repeated three times. The resulting residue was purified by gel column chromatography (Sephadex G-25, H₂O) to obtain an asparagine-linked oligosaccharaide having Fmoc group deprotected.

The above compound (6 mg, 2.58 μmoles) was dissolved in water (300 μl), and sodium bicarbonate (2.1 mg, 24.9 μmoles) was added to the solution. A solution of D-(+)-biotinylsuccinimide (4.2 mg, 12.3 μmoles) in dimethylformamide (300 μl) was added to the mixture, followed by reaction at room temperature for 20 minutes. The disappearance of the starting material was confirmed by TLC (isopropanol:1M ammonium acetate aqueous solution=3:2), and the reaction mixture was concentrated using an evaporator. The residue was purified with a gel column chromatography (Sephadex G-25, water), affording the following biotinated 3-branched asparagine-linked oligosaccharide derivative (6.2 mg, 94%).

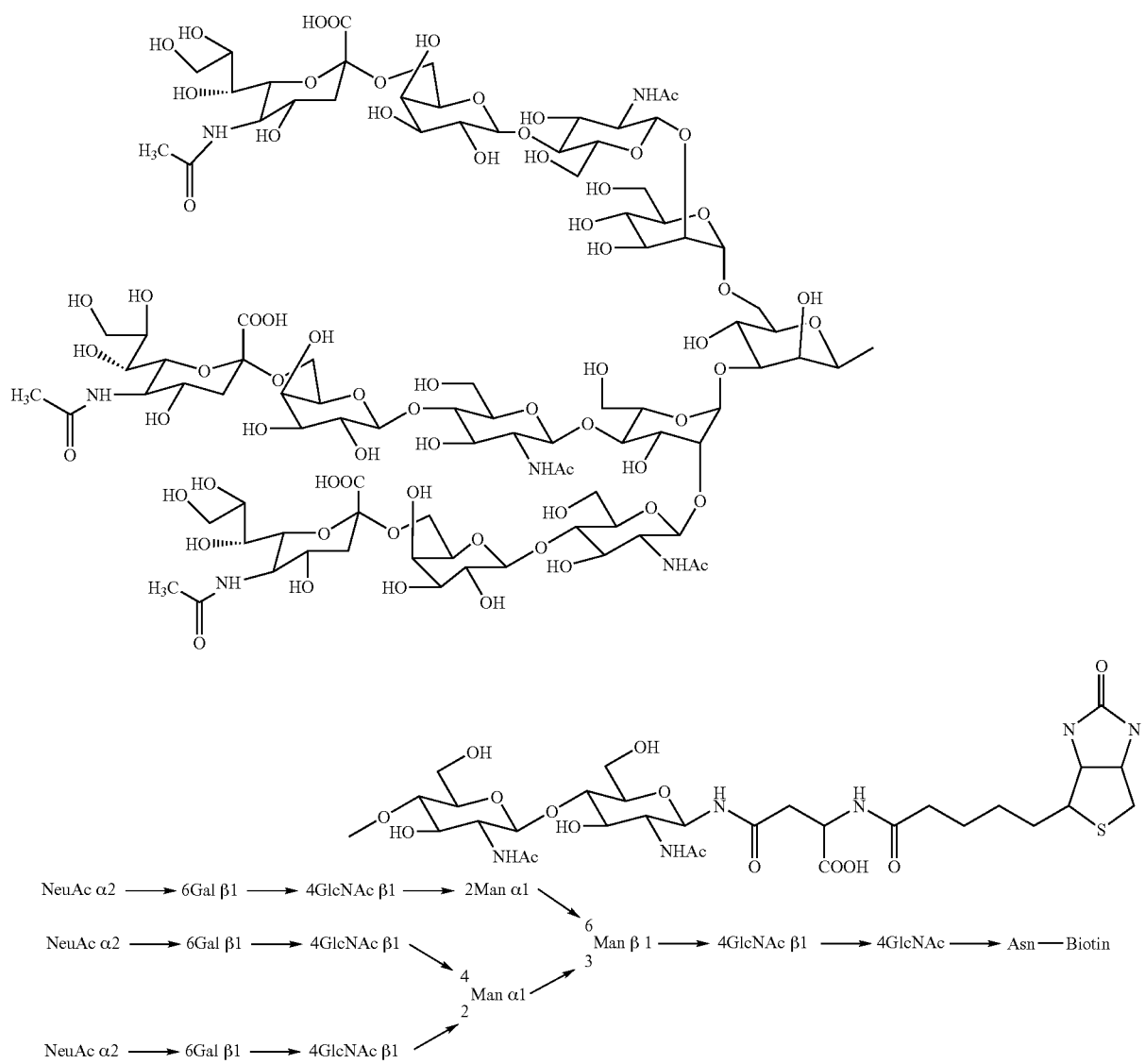

EXAMPLE 4

FITC Bonding

An asparagine-linked oligosaccharide having Fmoc group deprotected was obtained in the same manner as in Example 3. The above compound (1.4 mg, 0.60 μmol) was dissolved in 70 μl of purified water, and 70 μL of acetone and NaHCO$_3$ (0.76 mg, 9 μmoles) were added thereto and stirred at room temperature. Fluorescein isothiocyanate (FITC, 0.95 mg, 2.4 mmoles, product of Sigma Corp.) was added to the solution and the mixture was stirred for about 2 hours. After 2 hours, the completion of the reaction was confirmed by TLC, acetone was removed at a reduced pressure and the remaining aqueous solution was purified by gel column chromatography (Sephadex G-25, H$_2$O) to collect desired fraction. The fraction was concentrated and purified by HPLC (YMC-pack ODS-AM, SH-343-5AM, 20×250 mm, AN/25 mM AcONH$_4$ buffer=10/90, 7.5 ml/min., wave length: 274 nm). The fraction obtained was concentrated and desalted by gel column chromatography (Sephadex G-25, H$_2$O). The desired fraction was collected, concentrated and freeze-dried to obtain the following fluoresceined (FITC-bonded) 3-branched asparagine-linked oligosaccharide derivative (1.2 mg, 73.5% yield).

10 times the biotin bonding ability) was dissolved in distilled water to obtain 1000 μl solution. The solution thus adjusted was placed into the wells of 96-well BD BioCoat Streptavidin (product of BD Bioscience Corp. for bioassay, bonding ability: 5 ng/well) in an amount of 10 μl/well, and the wells were washed with distilled water three times to prepare a microplate. The bonding yield of the biotinated oligosaccharide was at least 95%. The fixation rate was calculated from the quantity of oligosaccharide remaining unfixed.

EXAMPLE 6

Preparation of Affinity Column

Avidin-coated beads (product of Hitachi Software Engineering Co., Ltd., XMAP LumAvidin Development Micro-

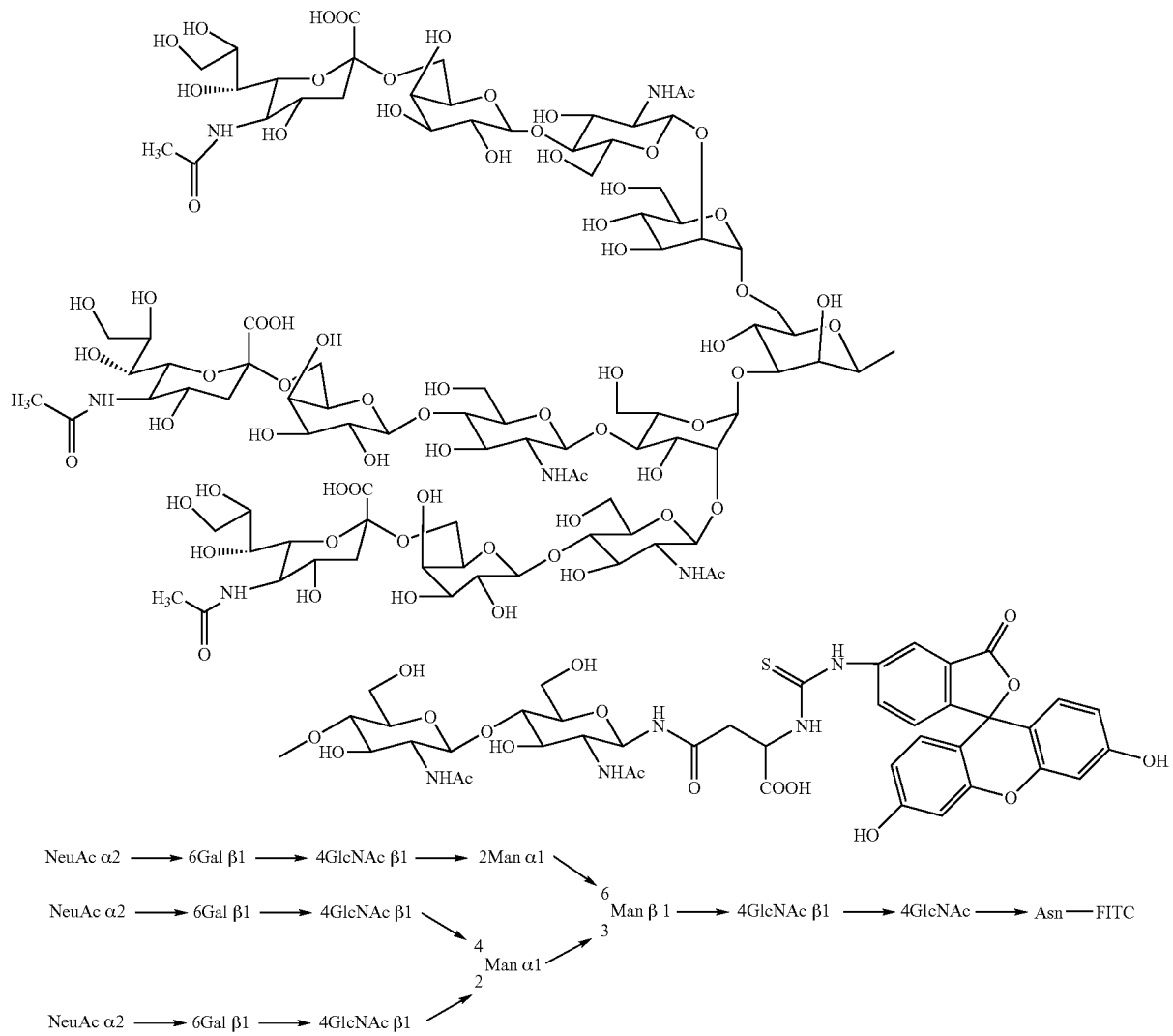

EXAMPLE 5

Preparation of Microplate

The biotinated asparagine-linked oligosaccharide of Example 3 in an amount of 100 μg (corresponding to about spheres 1 ml) in an amount of 10 ml and 30 mg of biotinated asparagine-linked oligosaccharide of Example 3 were stirred in the form of a slurry, and the beads were filtered off and washed. Washing was done using distilled water in an amount twice the volume of the beads, three times on filter paper. Fixation was confirmed from the amount of remaining biotinated oligosaccharide collected by washing. Subsequently, 10 ml of beads having the biotinated asparagine-linked oligosaccharide fixed thereto and 30 ml of distilled water were packed in the form of a slurry into an open chromatographic glass column (20 mm in diameter, 300 mm in length) to produce an affinity column.

INDUSTRIAL APPLICABILITY

The present invention provides 3-branched asparagine-linked oligosaccharide derivatives, as isolated and useful in the field of developing pharmaceutical products, in large quantities with much greater ease than the prior art. In addition to these derivatives, the invention further provides isolated 3-branched asparagine-linked oligosaccharides and 3-branched oligosaccharides in large quantities with much greater ease than conventionally.

Utilizing the specificity of biotin-avidin bond, the invention further provides an oligosaccharide microchip easily merely by reacting a plurality of biotinated oligosaccharides on an avidinated microplate, whereby protens can be clarified which have ability to bond to a specific oligosaccharide.

In order to isolate and purify a specific protein, a specific biotinated oligosaccharide is bonded and fixed to an avidinated affinity column, and a mixture containing a protein having ability to specifically bond to the biotinated oligosaccharide is passed through the column, whereby the desired protein only can be isolated.

The FITC-bonded asparagine-linked oligosaccharide obtained by the invention is useful for the research on acceptors of saccharides in the living body tissues and for the research on the sugar bond specificity of lectin.

The invention claimed is:

1. A 3-branched asparagine-linked oligosaccharide derivative of the formula (1) wherein the nitrogen of amino group of asparagine is modified with a lipophilic protective group, biotin group or FITC group

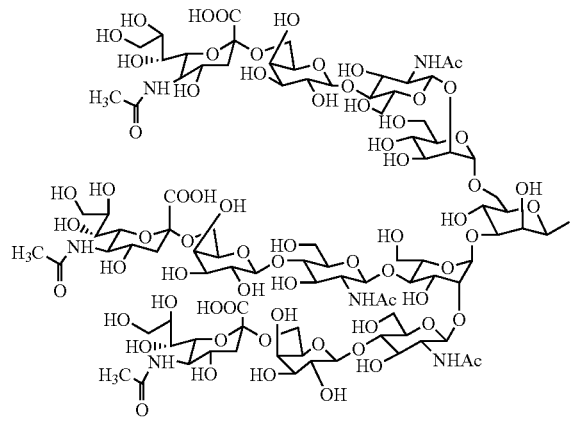

-continued

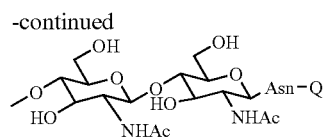

wherein Q is a lipophilic protective group, biotin group or FITC group.

2. A 3-branched asparagine-linked oligosaccharide derivative according to claim 1 which contains at least one fucose linked to an N-acetylglucosamine on the nonreducing terminal side of the 3-branched asparagine-linked oligosaccharide of the derivative.

3. A 3-branched asparagine-linked oligosaccharide derivative according to claim 1 or 2 wherein the lipophilic protective group is an Fmoc group.

4. A process for preparing a 3-branched asparagine-linked oligosaccharide derivative having a lipophilic protective group introduced thereinto, the process being characterized in that the process includes:

(a) the step of introducing a lipophilic protective group into one or at least two 3-branched asparagine-linked oligosaccharides as contained in a mixture thereof to obtain a 3-branched asparagine-linked oligosaccharide derivative mixture, and (b) the step of subjecting to chromatography the 3-branched asparagine-linked oligosaccharide derivative mixture or a mixture obtained by hydrolyzing the 3-branched asparagine-linked oligosaccharide derivative or derivatives contained in the 3-branched asparagine-linked oligosaccharide derivative mixture to separate the derivative or derivatives.

5. A process for preparing a 3-branched asparagine-linked oligosaccharide derivative modified with a biotin group characterized by biotinating a 3-branched asparagine-linked oligosaccharide.

6. A process for preparing a 3-branched asparagine-linked oligosaccharide derivative modified with an FITC group characterized by bonding FITC to a 3-branched asparagine-linked oligosaccharide.

7. A process for preparing a 3-branched asparagine-linked oligosaccharide characterized by removing a lipophilic protective group, biotin group or FITC group from a 3-branched asparagine-linked oligosaccharide derivative.

8. A microplate having immobilized thereto a biotinated 3-branched asparagine-linked oligosaccharide of claim 1 or 2.

9. An affinity column having immobilized thereto a biotinated 3-branched asparagine-linked oligosaccharide of claim 1 or 2.

* * * * *